(12) United States Patent
Ellwood et al.

(10) Patent No.: US 6,900,359 B2
(45) Date of Patent: May 31, 2005

(54) PRODUCTION OF 3-ALKYLCYCLOALKANOLS

(75) Inventors: Simon Ellwood, Kent (GB); Jan Thomas Haines, Kent (GB); Christopher Paul Newman, Kent (GB)

(73) Assignee: Quest International Services B.V., Naarden (NL)

( * ) Notice: Subject to any disclaimer, the term of this patent is extended or adjusted under 35 U.S.C. 154(b) by 0 days.

(21) Appl. No.: 10/344,531

(22) PCT Filed: Aug. 10, 2001

(86) PCT No.: PCT/GB01/03619

§ 371 (c)(1),
(2), (4) Date: Sep. 8, 2003

(87) PCT Pub. No.: WO02/14255

PCT Pub. Date: Feb. 21, 2002

(65) Prior Publication Data

US 2004/0030193 A1 Feb. 12, 2004

(30) Foreign Application Priority Data

Aug. 14, 2000 (EP) .............................................. 00306953

(51) Int. Cl.$^7$ ................................................. C07L 35/08

(52) U.S. Cl. ...................................... 568/834; 568/822

(58) Field of Search ................................ 568/834, 822

(56) References Cited

U.S. PATENT DOCUMENTS

| | | | | | |
|---|---|---|---|---|---|
| 4,326,997 A | * | 4/1982 | Willis et al. | ................... | 512/23 |
| 4,719,041 A | * | 1/1988 | Schaper et al. | ............. | 510/106 |
| 5,268,356 A | * | 12/1993 | Decorzant et al. | ............. | 512/23 |
| 6,313,087 B1 | * | 11/2001 | Rossiter | ........................ | 512/25 |

FOREIGN PATENT DOCUMENTS

WO 98/47842 10/1998

OTHER PUBLICATIONS

A. Jirgensons, et al., "Synthesis and structure–affinity relationships of 1,3,5–alkylsubstituted cyclhexylamines binding at NMDA receptor PCP site", European Journal of Medicinal Chemistry, vol. 35, No. 6, Jun. 2000, pp. 555–565.

T. Ma, et al., "An Efficient Method for the Synthesis of 4,5–Disubstituted Catechols", Bulletin of the Chemical Society of Japan, vol. 73, No. 3, Mar. 2000, pp. 747–748.

J. Tanaka, et al., "Studies on aromatic sesquiterpenes. XII", Bulletin of the Chemical Socity of Japan. vol. 63, No. 1, Jan. 1990, pp. 272–274.

E.E. Harris, et al., "Reaction of hardwood lignin with hydrogen", Journal of the American Chemical Society, vol. 60, No. 6, Jun. 1938, pp. 1467–1470.

J. Vrkoč, et al., "On terpenes. CXXIII. On the structure of calacone, a new sesquiterpenic ketone from the sweet–flag oil", vol. 26, No. 5, May 1961, pp. 1343–1349.

* cited by examiner

Primary Examiner—Michael L. Shippen
(74) Attorney, Agent, or Firm—Morgan, Lewis & Bockius LLP (57) ABSTRACT

A method of making a 3-alkylcycloalkanol of formula 2: where $R_1$ represents a methyl or ethyl group, $R_2$ represents hydrogen, $R_3$ represents an ethyl, propyl, butyl, isobutyl or isoamyl group, $R_4$ represents hydrogen and $R_5$ represents hydrogen, or a methyl, ethyl, propyl, isobutyl or isoamyl group comprises the following steps: (1) carrying out an electrophilic substitution reaction of an alkyl group or precursor thereof, on an ortho-substituted alkylbenzene compound of formula 3: where $R_6$ represents hydrogen, or a methyl or ethyl group; (2) hydrogenating the reaction product of step (1); (3) performing an elimination reaction on one or more reaction products of step (2) to produce one or more alkene products; and (4) hydrating the one or more alkene products of step (3) to provide a 3-alkylcycloalkanol of formula 2. The electrophilic substitution reaction of step (1) may be a Friedel-Crafts acylation, e.g. using an isopropyl ketone precursor, or a Friedel-Crafts alkylation, e.g. using an isobutyl group. The 3-alkylcycloalkanols, especially 3-(2-methylpropyl)-1-methylcyclohexanol, are useful fragrance materials and find use in perfumes and perfumed products.

16 Claims, 1 Drawing Sheet

Figure 1

PRODUCTION OF 3-ALKYLCYCLOALKANOLS

FIELD OF THE INVENTION

This invention concerns the production of 3-alkylcycloalkanols, which are useful fragrance materials used in perfumes and perfumed products.

BACKGROUND TO THE INVENTION

WO 98/47842 describes and claims novel 3-alkylcycloalkanols of formula 1:

Formula 1 where $R_1$ represents a methyl, ethyl or propyl group; $R_2$, $R_4$ and $R_5$ independently represent hydrogen or a methyl group; $R_3$ represents a saturated hydrocarbon group with 4–8 carbon atoms, provided that the first carbon atom of this hydrocarbon group is not a tertiary carbon atom; and n represents the numbers 1, 2 and 3. These 3-alkylcycloalkanols are useful fragrance materials which find use in perfumes and perfumed products. One particularly preferred material is 1-methyl-3-(2-methylpropyl) cyclohexan-1-ol (also known as 3-(2-methylpropyl)-1-methylcyclohexanol) which has the structure:

i.e. $R_1=CH_3$, $R_2=H$, $R_3$=isobutyl, $R_4=H$, $R_5=H$ and n=2 in formula 1.

The present invention concerns a novel process for producing certain of the 3-alkylcycloalkanols of formula 1, including 1-methyl-3-(2-methylpropyl) cyclohexan-1-ol.

SUMMARY OF THE INVENTION

In one aspect of the present invention provides a method of making a 3-alkylcycloalkanol of formula 2:

Formula 2 where $R_1$ represents a methyl or ethyl group, $R_2$ represents hydrogen, $R_3$ represents an ethyl, propyl, butyl, isobutyl or isoamyl group, $R_4$ represents hydrogen and $R_5$ represents hydrogen, or a methyl, ethyl, propyl, isobutyl or isoamyl group, comprising the following steps:

(1) carrying out an electrophilic substitution reaction of an alkyl group or precursor thereof, on an ortho-substituted alkylbenzene compound of formula 3:

Formula 3 where $R_6$ represents hydrogen, or a methyl or ethyl group;
(2) hydrogenating the reaction product of step (1);
(3) performing an elimination reaction on one or more reaction products of step (2) to produce one or more alkene products; and
(4) hydrating the one or more alkene products of step (3) to provide a 3-alkylcycloalkanol of formula 2.

The electrophilic substitution reaction of step (1) may be a Friedel-Crafts alkylation, e.g. using an isobutyl group, or a Friedel-Crafts acylation, e.g. using an isopropyl ketone precursor.

The Friedel-Crafts alkylation reaction provides for direct alkylation of the ortho-substituted alkylbenzene ring, giving a product of formula 4:

Formula 4

The alkylation reaction may be carried out using an appropriate alkene, alcohol or alkyl halide and may be performed in a generally conventional manner, as is known to those skilled in the art. Alternatively, the reaction may be carried out using allylic halides or allylic alcohols which will produce an allylic substituent on the starting material, i.e. a Friedel-Crafts allyation reaction.

The Friedel-Crafts acylation reaction provides for the addition of a precursor of an alkyl group to the ortho-substituted alkylbenzene ring, typically giving a product of formula 5:

Formula 5

The acylation reaction may be carried out using an appropriate acid, anhydride or acid halide and may be performed in a generally conventional manner, as is known to those skilled in the art.

There are various advantages and disadvantages associated with the alkylation and acylation routes which vary according to circumstances including the material to be made, starting materials used and reaction scale. For any particular set of circumstances the advantages and disadvantages can be compared and a favoured route selected, bearing in mind factors including cost, safety and product odour quality. For example, the initial product of the alkylation reaction is generally more reactive than the starting material and further alkylation may occur to yield various polyalkylated products. The resulting complex reaction product mixture therefore generally requires careful and expensive purification and may typically give poor overall yields of the desired product. When the alkyl group is an isobutyl group, this problem is greatly exacerbated, as the alkylating agent (i.e. the isobutyl cation) rearranges (wholly or in part) under the reaction conditions, resulting in t-butylation of the ortho-substituted alkylbenzene starting material.

In general, the Friedel-Crafts acylation reaction is a much cleaner reaction compared with a Friedel-Crafts alkylation reaction, because the primary reaction product does not react further. However, this reaction may have its own disadvantages. For example, the substituted acetophenone intermediate requires further processing (in the present case by hydrogenation) to obtain the desired alkylated product of formula 4. Further, for environmental reasons it is appropriate to use phenolic ethers rather than cheaper phenols, as acylation of phenols requires more than 2 moles of Lewis acid per mole of phenol which is environmentally unacceptable as a manufacturing process. However, in some circumstances such disadvantages are considered to be greatly outweighed by the advantage of producing a cleaner reaction product.

The acylation of phenolic ethers may be carried out using trace amounts of trifluoromethanesulfonic acid (triflic acid), perchloric acid or fluoroboric acid as catalysts. Preferably the reaction is conveniently carried out using trifluoromethanesulfonic acid (triflic acid) as catalyst. Use of such catalysts for this purpose is not conventional and not generally known.

Suitable acylating agents for use herein include appropriate anhydrides, which may be mixed anhydrides although it is preferred to use symmetric anhydrides (e.g. isobutyric anhydride), acid halides (e.g. isobutyryl chloride) and, for phenolic ethers, acids (e.g. isobutyric acid). Preferably, the acylating agent is an anhydride. Acids have been found to react cleanly in the absence of a drying agent in a Friedel-Crafts acylation reaction, however, they were only reactive to a limited extent: by performing such reactions in the presence of a suitable drying agent, it is thought that the reactions may proceed to completion. Acid chlorides have been found by the present inventors to be of limited usefulness in the method according to the present invention, as they produce chlorine impurities which are not compatible with the hydrogenation catalysts of step (2).

The hydrogenation reaction at step (2) generally proceeds via a one stage procedure when the electrophilic substitution reaction is a Friedel-Crafts alkylation. This hydrogenation may be carried out in generally known manner using a catalyst such as palladium, rhodium, ruthenium, platinum or nickel, under suitable conditions of pressure and temperature. The material of formula 4 is thereby converted into a mixture of ethers and alcohols of formulas 6 and 7, respectively, as follows:

Formula 4    Formula 6

Formula 7

The hydrogenation reaction of step (2) is typically carried out as a two stage process when the electrophilic substitution reaction is a Friedel-Crafts acylation, initially converting the material of formula 5 into that of formula 4, followed by conversion to the ethers and the alcohols of formulas 6 and 7, respectively. It is generally highly desirable to carry out the two stage process sequentially. The reaction product produced by the Friedel-Crafts acylation reaction in one preferred embodiment herein is 1-(4-alkoxy-3-alkylphenyl)-2-methyl-1-propanone. Thus, the 2-methyl-1-propanone substituent on the phenyl ring is conveniently converted to the desired isobutyl group during the first stage of the hydrogenation reaction.

Different catalysts and/or reaction conditions may be required for the different hydrogenation stages. Suitable catalysts for the first stage include palladium, platinum, rhodium and ruthenium, in each case supported on carbon or other appropriate support. A particularly efficient two stage hydrogenation reaction has been devised using the same catalyst (palladium supported on carbon) in the same vessel, by varying pressure and temperature appropriately. Stage 1 is conveniently performed at a temperature of about 100° C. and a pressure of about 20 bar gauge for a time of about 1 hour, with stage 2 being at a temperature of about 140–150° C., a pressure of about 48 bar gauge and for a time of about 6–10 hours.

A hydroxy acid co-catalyst is also conveniently employed in one or both hydrogenation stages. The preferred co-catalyst for use herein in view of its ease of handling is lactic acid, as an 85% solution in water. The use of a hydroxy acid co-catalyst is not known in the context of conversion of the material of formula 4 to formulas 6 and 7. This novel use of a co-catalyst was found to demonstrate two unexpected and surprising effects: 1) the presence of a co-catalyst in the reaction mixture advantageously accelerated the rate of hydrogenation of the phenyl ring under the conditions employed; and 2) the hydroxy acid co-catalyst catalysed the hydrolysis of intermediate vinyl ethers formed during the course of the hydrogenation reaction, yielding alcohols in the final reaction products. The presence of such alcohols may be advantageous in the elimination reaction of step (3), as alcohols typically react more readily than ethers. The quantity of alcohols formed is dependent on the amount of water in the system and it may be advantageous to add more than is readily present in the catalyst and co-catalyst.

Thus, in general, the reaction products of hydrogenation step (2) are a complex mixture of alcohols and ethers which occur in numerous isomeric forms. The relative amounts and stereo-isomeric composition of alcohol and ether are dependent on the precise conditions used for their formation.

The elimination reaction of step (3) may be performed on either an alcohol or an ether reaction product of step (2), or mixtures of alcohols and ethers. Preferably, the elimination reaction is performed on the reaction products of step (2) which are conveniently a mixture of alcohols and ethers to produce alkene products.

The elimination reaction of step (3) may be performed in generally known manner, e.g. using catalysts such as triflic acid, 4-methylbenzenesulphonic acid (pTSA) or phosphoric acid. The choice of catalyst for the elimination reaction will depend upon the proportion of isomers in the cis- and trans-configuration, desirably in any particular mixture of alcohols and ethers, where 'cis' and 'trans' for the ensuing discussion are not specified according to conventional IUPAC nomenclature, but are specified according to the relative positions of the hydroxy or alkoxy substituents of the cyclohexane ring, and the adjacent $R_1$ group.

The hydration reaction of step (4) may be performed in generally known manner, e.g. using sulphuric acid. Advantageously a small amount of the desired end product is added to act as a phase transfer agent and help the reaction initiate.

The invention may be used for production of a wide range of 3-alkylcycloalkanols by selection of suitable starting materials, on a range of different manufacturing scales. As noted above the choice of using alkylation or acylation routes will depend on the particular circumstances and it will be understood by those skilled in the art that the choice of route depends both on the desired product and the scale of manufacture.

For relatively small scale manufacture of materials, e.g. 3-(2-methylpropyl)-1-methylcyclohexanol, acylation of phenolic ethers is currently favoured.

One preferred embodiment of the method of the invention, appropriate e.g. for small scale manufacture of 3-(2-methylpropyl)-1-methylcyclohexanol, may be illustrated by the following reaction sequence:

1) carrying out an electrophilic substitution reaction, where the electrophilic substitution reaction is a Friedel-Crafts acylation, on an ortho-substituted alkylbenzene compound of formula 3

Formula 3 with an anhydride of formula 8

Formula 8 where $R_7$ and $R'_3$ are each independently methyl, ethyl or isopropyl, to produce a product of formula 5 as follows:

2) hydrogenating the product of formula 5 to produce a mixture of ethers of formula 6 and alcohols of formula 7, via an intermediate of formula 4, as follows:

Formula 5    Formula 4

Formula 6    Formula 7

3) performing an elimination reaction on the ethers of formula 6 and the alcohols of formula 7 to produce alkene isomers including those of formula 9 and formula 10, with trace amounts of an alkene of formula 11, as follows:

Formula 6    Formula 7

Formula 9    Formula 10

Formula 11 where $R_8$ represents $CH_2$ or $CHCH_3$, 4) hydrating the alkene products of step (3) to produce an alcohol product of formula 2 as follows:

By varying $R_1$, $R'_3$ and $R_5$ in the starting materials used in step (1), so a desired end product of formula 2 can be produced.

For example, using 1-methoxy-2-methylbenzene (methyl anisole) ($R_1$=methyl, $R_5$=hydrogen and $R_6$=methyl in Formula 3) and 2-methylpropanoic anhydride ($R'_3$=isopropyl and $R_7$=isopropyl in Formula 8), 1-methyl-3-(2-methylpropyl) cyclohexan-1-ol can be produced.

$R'_3$ and $R_7$ are preferably the same, and are desirably both isopropyl, so that the anhydride of formula 8 is symmetric, although mixed (asymmetric) anhydrides may be used.

$R_6$ is preferably a methyl group.
$R_1$ is preferably a methyl group.
$R_5$ is preferably hydrogen.

Thus, in one preferred embodiment of the present invention, the ortho-substituted alkylbenzene compound of formula 3 is 1-methoxy-2-methylbenzene (methyl anisole).

The method of the invention can employ very cheap, readily available starting materials and use these to produce useful fragrance materials in an efficient, environmentally effective and commercially advantageous way.

The invention also includes within its scope 3-alkylcycloalkanols of formula 2 produced by the method of the invention, and perfumes and perfumed products including these materials. The invention will be further described, by way of illustration, in the following Example, which describes production of 3-(2-methylpropyl)-1-methylcyclohexanol by the method of the invention and with reference to the accompanying drawing in which:

GC/GLC conditions utilised for analyses in the following Examples:

| | |
|---|---|
| GC: | Hewlett Packard HP 6890 Gas Chromatograph |
| Column: | HP-5 (SE54) 30 m × 0.32 mm (internal diameter) × 0.25 μm df supplied by Hewlett Packard |
| Carrier Gas: | Hydrogen |
| Solvent/Injection Volume: | Acetone, 0.2 μl |
| Injector: | 220° C., split 60:1 |
| Detector: | FID, 280° C. |
| Temperature Prog.: | 70° C. (initial oven temperature), hold for 3 minutes, ramp at 10° C./min to 100° C., then ramp at 25° C./min to 280° C. and hold for 4 minutes. |

EXAMPLE 1

Stage 1. Friedel Crafts Acylation

Experimental 1-methoxy-2-methylbenzene (methyl anisole) (261 kg, 98.6% pure, 2.109 kmol) and trifluoromethanesulphonic acid (triflic acid) (326 g, 2.17 mol) (catalyst) were charged to a 1360 liter general purpose glass-lined reactor. The mixture was heated under nitrogen with stirring to a temperature of 150° C. Once at temperature, 1-methylpropanoic anhydride (365 kg, 2.31 kmol) was charged gradually to the reactor over a period of two hours while maintaining the reaction temperature at 150° C. The mixture was stirred for a further one and a half hours at this temperature. After cooling to 40° C. the catalyst was neutralised with solid sodium carbonate (230 g, 2.16 mol) and the 2-methylpropanoic acid by-product was distilled off under reduced pressure (30 mBar) up to a pot temperature of 120° C. The resultant material was washed twice with a 5% w/w sodium carbonate solution (60 kg) to leave the crude product, 1-(4-methoxy-3-methylphenyl)-2-methyl-1-propanone, 93.9% pure by GC rpa. (385 kg, 1.88 kmol, 89.2% theoretical yield by analysis based on 1-methoxy-2-methylbenzene).

Distillation

The crude material (381.4 kg, 1.86 kmol) was purified by distillation under reduced pressure through a 5 theoretical plate packed column. The product, 1-(4-methoxy-3-methylphenyl)-2-methyl-1-propanone (345.5 kg, purity 97.7% rpa, 1.76 kmol) was collected at 137–140° C. at 8 mBar and crystallised on standing with a melting point of 22° C. Thus, the overall yield of distilled product was 84.1% based on 1-methoxy-2-methylbenzene.

1-methyl-2-methylbenzene + 1-methylpropanoic anhydride →

1-(4-methoxy-3-methylphenyl)-2-methyl-1-propanone + 2-methylpropanoic acid

Stage 2. Hydrogenation

Experimental

1-(4-methoxy-3-methylphenyl)-2-methyl-1-propanone (60.0 kg, 97.3% pure by GC, 0.304 kmol) made as described above was charged to a high-pressure 100 liter reactor fitted with a stirrer and hydrogen supply. Distilled water (25.0 kg, 1.389 kmol), lactic acid co-catalyst, 85% aq. solution (2.0 kg, 18.9 mol) and hydrogenation catalyst (5% palladium on charcoal Type 87L paste ex Johnson Matthey, 1.2 kg) were charged to the reactor. After purging with nitrogen and hydrogen, for the first stage of hydrogenation, the stirring mixture was placed under a hydrogen atmosphere of 20 bar and taken to a temperature of 100° C. over a period of 1 hr, maintaining the pressure of 20 bar gauge with the addition of more hydrogen gas. This temperature and pressure was maintained for a further hour until hydrogen addition effectively ceased (<15 g/hr). For the second stage of hydrogenation, the pressure was raised to 48 bar gauge before heating to 140° C.–150° C. This temperature and pressure was maintained for about 6–10 hours (with the reaction time depending on the quality of both the catalyst and feedstock) until hydrogen addition effectively ceased. After cooling to room temperature the pressure was released and, after nitrogen purging, the mixture was filtered to remove the hydrogenation catalyst. The aqueous layer was separated from the crude product (55.4 kg).

Detailed GLC analysis of the crude product showed an isomeric mixture of 4-(2-methylpropyl)-1-methoxy-2-methylcyclohexanes and 4-(2-methylpropyl)-2-methylcyclohexanols constituting 93.3% rpa of the product. According to this analysis, these desired products totalled 0.29 kmol, which corresponded to a 92.8% theoretical yield based on 1-(4-methoxy-3-methylphenyl)-2-methyl-1-propanone.

Distillation

Distillation is not essential, but usefully the product ethers and alcohols are together separated from water, light heads and residues by a simple distillation up a short, packed column of about 5 theoretical plates: Typically, crude 4-(2-methylpropyl)-1-methoxy-2-methylcyclohexane/4-(2-methylpropyl)-2-methylcyclohexanol (55.4 kg, 93.3% rpa pure by GC, 0.29 kmol) yielded an isomeric mixture of 4-(2-methylpropyl)-1-methoxy-2-methylcyclohexanes and 4-(2-methylpropyl)-2-methylcyclohexanols (52.4 kg, 96.0% rpa pure by GC, 0.28 kmol) having a boiling range of 98–116° C./30 mBar.

1-(4-methoxy-3-methylphenyl)-2-methyl-1-propanone

4-(2-methylpropyl)-1-methoxy-2-methylbenzene 4-(2-methylpropyl)-1-methoxy-2-methylcyclohexane 4-(2-methylpropyl)-2-methylcyclohexanol The ethers occur in a number of different isomeric forms as follows:

(1a)(1S,2R,4R)4-(2-methylpropyl)-1-methoxy-2-methylcyclohexane    (1b)(1R,2S,4S)4-(2-methylpropyl)-1-methoxy-2-methylcyclohexane (2a)(1S,2S,4R)4-(2-methylpropyl)-1-methoxy-2-methylcyclohexane    (2b)(1R,2R,4S)4-(2-methylpropyl)-1-methoxy-2-methylcyclohexane

(3a)(1R,2S,4R)4-(2-methylpropyl)-1-methoxy-2-methylcyclohexane    (3b)(1S,2R,4S)4-(2-methylpropyl)-1-methoxy-2-methylcyclohexane (4a)(1R,2R,4R)4-(2-methylpropyl)-1-methoxy-2-methylcyclohexane    (4b)(1S,2S,4S)4-(2-methylpropyl)-1-methoxy-2-methylcyclohexane The alcohols occur in a number of corresponding isomeric forms as follows:

(5a)(1S,2R,4R)4-(2-methylpropyl)-2-methylcyclohexanol    (5b)(1R,2S,4S)4-(2-methylpropyl)-2-methylcyclohexanol (6a)(1S,2S,4R)4-(2-methylpropyl)-2-methylcyclohexanol  
(6b)(1R,2R,4S)4-(2-methylpropyl)-2-methylcyclohexanol  
(7a)(1R,2S,4R)4-(2-methylpropyl)-2-methylcyclohexanol  
(7b)(1S,2R,4S)4-(2-methylpropyl)-2-methylcyclohexanol  
(8a)(1R,2R,4R)4-(2-methylpropyl)-2-methylcyclohexanol  
(8b)(1S,2S,4S)4-(2-methylpropyl)-2-methylcyclohexanol

Stage 3. Elimination
Experimental

An isomeric mixture of 4-(2-methylpropyl)-1-methoxy-2-methylcyclohexanes and 4-(2-methylpropyl)-2-methylcyclohexanols (46.3 kg, 92.6% rpa pure by GC, ~0.24 kmol) made as described above, 4-methylbenzenesulphonic acid monohydrate (pTSA catalyst) (1.4 kg, 7.4 mol) and cyclohexane (10.0 kg) were charged to a 100 liter glass-lined general purpose reactor. The stirred mixture was heated to a temperature of 150° C. under a nitrogen atmosphere. The cyclohexane/water/methanol azeotrope was removed in the Dean & Stark, with the upper cyclohexane layer being returned to the flask. The quantity of cyclohexane was adjusted to maintain the flask temperature at 150° C.–155° C. These conditions were maintained for 8 hours. After cooling to 40° C. the mixture was washed twice with a 5% w/w sodium carbonate solution (9.0 kg) and dehydrated to leave the crude product 3-(2-methylpropyl)-1-methyl-1-cyclohexene/5-(2-methylpropyl)-1-methyl-1-cyclohexene (typically in the ratio 1:2), 40.4 kg, 66.9% rpa pure by GC (27.0 kg, 0.18 kmol) with trace amounts of 1-methylidene-3-(2-methylpropyl)cyclohexane, and unreacted starting materials 9.6% rpa by GC (3.9 kg, 0.02 kmol). Thus, the chemical yield of this reaction was 75% and the selectivity was 82%.

Distillation

The crude product (80.4 kg) from two such reactions, containing 64.5% rpa pure by GC (0.34 kmol) of the desired alkenes was purified by careful fractional distillation under reduced pressure through a 30 theoretical plate packed column at a 20:1 reflux ratio. The mixture of 3-(2-methylpropyl)-1-methyl-1-cyclohexene and 5-(2-methylpropyl)-1-methyl-1-cyclohex was collected in the range 88–93° C./32–40 mBar. The purified product (61 kg) contained 81.5% rpa of the desired alkenes corresponding to a distillation yield of 96%. The product is a liquid at normal temperatures.

The unreacted starting materials remained in the distillation residues.

4-(2-methypropyl)-1-methoxy-2-methylcyclohexane  
4-(2-methypropyl)-2-methylcyclohexanol  
5-(2-methylpropyl)-1-methyl-1-cyclohexene  
1-methylidene-3-(2-methylpropyl)cyclohexane  
3-(2-methylpropyl)-1-methyl-1-cyclohexene  
+ methanol + H$_2$O

Stage 4. Hydration
Experimental

A mixture of 3-(2-methylpropyl)-1-methyl-1-cyclohexene and 5-(2-methylpropyl)-1-methyl-1-cyclohexene (30.1 kg, "purity" 82.1% rpa, 0.16 kmol) together with a small amount of 1-methylidene-3-(2-methylpropyl)cyclohexane, made as described above was charged to a 100 liter glass-lined general purpose reactor. 3-(2-methylpropyl)-1-methylcyclohexanol (0.3 kg, 1.76 mol) was added (this small amount of the desired end product acts as a phase transfer agent and helps the reaction initiate). The stirred mixture was cooled to −5° C. and sulphuric acid, 76% w/w (20.4 kg, 0.158 kmol) was added slowly over 5 hours, maintaining the temperature in the range −6° C. to −3° C. The stirred mixture was held at this temperature range for a further hour after the acid addition. The mixture was slowly added to water (80.0 kg, 4.4 kmol) in a well-stirred quench vessel maintaining the temperature below 25° C., before separating the lower aqueous phase. The organic layer was washed with water (11.0 kg) while still maintaining the temperature below 25° C. The residual acid catalyst was neutralised by washing the reaction mixture with 5% sodium hydroxide solution (10.0 kg), maintaining a temperature below 30° C. The resultant product was washed twice with water (10.0 kg) at 50° C.–55° C. to leave the crude product (3-(2-methylpropyl)-1-methylcyclohexanol) (30.8 kg). GLC analysis showed that this crude product contained 52.55% rpa (0.095 kmol) of pure 3-(2-methylpropyl)-1-methylcyclohexanol, in the form of a mixture of trans and cis isomers. This corresponds to a chemical yield of 59.1% based on 3-(2-methylpropyl)-1-methyl-1-cyclohexene/5-(2-methylpropyl)-1-methyl-1-cyclohexene.

Distillation

The crude product (30.8 kg, 0.095 kmol) was purified by fractional distillation under reduced pressure through a packed column of about 15 theoretical plates. The product (3-(2-methylpropyl)-1-methylcyclohexanol (15.28 kg, 98.7% by GC rpa, 0.089 kmol) was collected at 98–100° C., 15 mBar. This gave an overall yield of 55.1% w/w of Perfumery Quality material based on 3-(2-methylpropyl)-1-methyl-1-cyclohexene/5-(2-methylpropyl)-1-methyl-1-cyclohexene. The product, 3-(2-methylpropyl)-1-methylcyclohexanol was a mixture of approximately 35–45% cis, and about 55–65% trans isomers. The product may solidify on standing with a melting point of 20–25° C.

Figure 1:
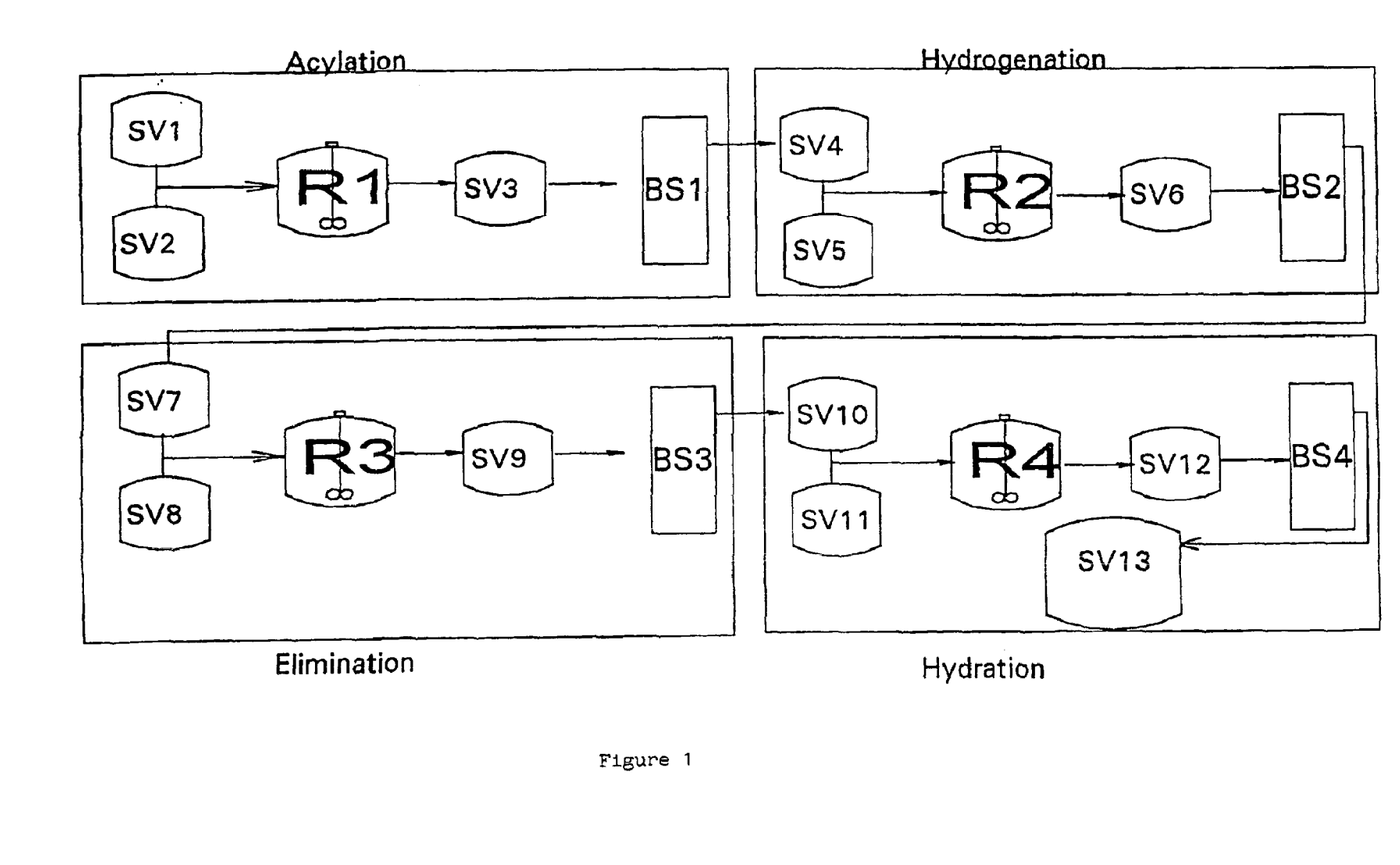
FIG. 1 is a schematic representation of a suitable layout on a manufacturing plant scale for production of 3-(2-methylpropyl)-1-methylcyclohexanol according to a preferred method of the invention.

FIG. 1 illustrates schematically the layout of apparatus in which the method of the above Example can be performed.

Referring to FIG. 1, the reagents employed in each step of the method are stored prior to use in respective storage vessels SV1 to SV13. The storage vessels will be sized according to the desired production scale and in their simplest form may be drums. The acylation, hydrogenation, elimination and hydration reactions are carried out in respective reactors R1 to R4. R1, R3 and R4 may be constituted by a single reactor or separate reactors depending on logistics. The reaction product(s) of each stage of the process are transferred to respective batch stills BS1 to BS4 for purification, with the number of batch stills depending on the number of reactors.

The reagents for the acylation reaction, 1-methoxy-2-methylbenzene and 1-methylpropanoic anhydride, are stored in storage vessels SV1 and SV2 respectively prior to addition to reactor, R1. The acylation stage is thus carried out in the acylation reactor, R1. The facilities for catalyst, sodium carbonate and wash addition are not shown. Following reaction completion, the crude washed and dehydrated product (1-(4-methoxy-3-methylphenyl)-2-methyl-1-propanone)) is transferred to storage vessel, SV3, prior to distillation in BS1. The distilled product is then transferred to storage vessel SV4.

The purified 1-(4-methoxy-3-methylphenyl)-2-methyl-1-propanone is transferred from SV4, together with lactic acid from SV5 and water and catalyst (not shown) to the hydrogenation reactor, R2. After hydrogenation, the filtered organics are transferred to storage vessel SV6 prior to distillation in batch still BS2. The distilled reaction products (4-(2-methylpropyl)-1-methoxy-2-methylcyclohe and 4-(2-methylpropyl)-2-methylcyclohexanol) are then transferred to storage vessel SV7.

The distilled hydrogenation products residing in storage vessel SV7 are added to the elimination reactor R3, followed by cyclohexane from SV8. The facilities for the addition of the pTSA catalyst solution are not shown. The crude, washed and dehydrated products are then transferred into storage vessel SV9, prior to distillation in batch still BS3. The distilled products (3-(2-methylpropyl)-1-methyl-1-cyclohexene/5-(2-methylpropyl)-1-methyl-1-cyclohexene together with a small amount of 1-methylidene-3-(2-methylpropyl) cyclohexane) are stored in storage vessel SV10.

The alkene feedstock is then transferred from storage vessel SV10 into hydration reactor, R4. To the reactor is further added sulfuric acid from storage vessel SV11. Following reaction, the crude washed and dehydrated product is then transferred to storage vessel, SV12 prior to distillation in batch still BS4. The distilled product (3-(2-methylpropyl)-1-methylcyclohexanol) is transferred to SV13 prior to distribution.

What is claimed is:

1. A method of making a 3-alkylcycloalkaflol of formula 2:

Formula 2 wherein $R_1$ represents a methyl or ethyl group, $R_2$ represents hydrogen, $R_3$ represents an ethyl, propyl, butyl, isobutyl or isoamyl group, $R_4$ represents hydrogen and $R_5$ represents hydrogen, or a methyl, ethyl, propyl, isobutyl or isoamyl group, comprising the following steps:

(1) carrying out an electrophilic substitution reaction of an alkyl group or precursor thereof, on an ortho-substituted alkylbenzene compound of formula 3:

Formula 3 wherein $R_6$ represents hydrogen, or a methyl or ethyl group;

(2) hydrogenating the reaction product of step (1);
(3) performing an elimination reaction on one or more reaction products of step (2) to produce one or more alkene products; and
(4) hydrating the one or more alkene products of step (3) to provide a 3-alkylcycloalkanol of formula 2.

2. A method according to claim 1, wherein the electrophilic substitution reaction of step (1) is a Friedel-Crafts alkylation.

3. A method according to claim 2, wherein the alkylating agent is an allylic alcohol or halide.

4. A method according to claim 2 or 3, wherein the hydrogenation reaction proceeds via a one stage procedure.

5. A method according to claim 1, wherein the electrophilic substitution reaction of step (1) is a Friedel-Crafts acylation.

6. A method according to claim 5, wherein the compound of formula 3 is a phenolic ether and the acylation reaction of step (1) is carried out using trifluoromethanesulfonic aid as catalyst.

7. A method according to claim 5 or 6, wherein the hydrogenation reaction of step (2) is carried out as a two stage process.

8. A method according to claim 7, wherein the two stage hydrogenation reaction is carried out using the same catalyst, comprising palladium supported on carbon, in the same vessel, by varying pressure and temperature appropriately.

9. A method according to claim 8, wherein the first stage hydrogenation is performed at a temperature of about 100° C. and a pressure of about 20 bar gauge for a time of about 1 hour, and the second stage hydrogenation is performed at a temperature of about 140–1500° C., a pressure of about 48 bar gauge and for a time of about 6–10 hours.

10. A method according to claim 1, wherein the hydrogenation of step (2) is performed catalytically.

11. A method according to claim 10, wherein the hydrogenation catalyst is selected from palladium, platinum, rhodium, ruthenium and nickel.

12. A method according to claim 10 or 11, wherein the hydrogenation reaction is performed using a hydroxy acid co-catalysti.

13. A method according to claim 1, wherein the elimination reaction of step (3) is performed employing 4-methylbenzenesulphonic acid as a catalyst.

14. A method of making a 3-alkylcycloalkanol of formula 2:

Formula 2 wherein $R_1$ represents a methyl or ethyl group, $R_2$ represents hydrogen, $R_3$ represents an ethyl, propyl, butyl, isobutyl or isoamyl group, $R_4$ represents hydrogen and $R_5$ represents hydrogen, or a methyl, ethyl, propyl, isobutyl or isoamyl group, comprising the following steps:

1) carrying out an electrophilic substitution reaction, where the electrophilic substitution reaction is a Friedel-Crafts acylation, on an ortho-substituted alkylbenzene compound of formula 3

Formula 3 wherein $R_6$ represents hydrogen, or a methyl or ethyl group with an anhydride of formula 8

Formula 8 wherein $R_7$ and $R'_3$ are each independently methyl, ethyl or isopropyl, to produce a product of formula 5 as follows:

Formula 5

2) hydrogenating the product of formula 5 to produce a mixture of ethers of formula 6 and alcohols of formula 7, via an intermediate of formula 4, as follows:

Formula 5          Formula 4

Formula 6          Formula 7

3) performing an elimination reaction on the ethers of formula 6 and the alcohols of formula 7 to produce alkene isomers including those of formula 9 and formula 10, with trace amounts of an alkene of formula 11, as follows:

Formula 6          Formula 7

Formula 9          Formula 10

Formula 11 wherein $R_8$ represents $CH_2$ or $CHCH_3$, 4) hydrating the alkene products of step 3 to produce an alcohol product of formula 2 as follows:

Formula 9          Formula 10

Formula 11          Formula 2

15. A method according to claim 14, wherein $R_1$=methyl, $R_5$=hydrogen and $R_6$=methyl in Formula 3 and R'3= isopropyl and $R_7$=isopropyl in Formula 8, resulting in production of 1-methyl-3-(2-methylpropyl)cyclohexan-1ol.

16. A method according to claim 12 wherein the hydroxy acid co-catalyst is lactic acid.

* * * * *